Figure 1:
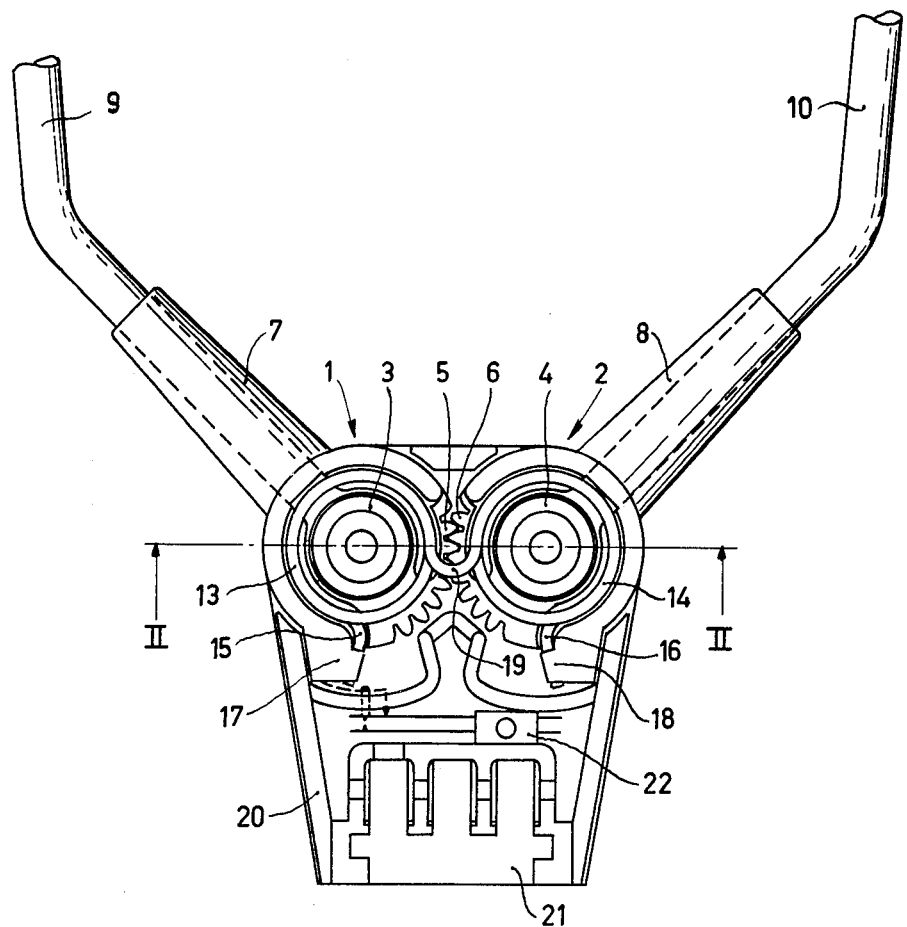

United States Patent [19]

Penning

[11] 4,277,654
[45] Jul. 7, 1981

[54] STETHOSCOPIC HEADPHONE SET

[75] Inventor: Cornelis Penning, Breda, Netherlands

[73] Assignee: U.S. Philips Corporation, New York, N.Y.

[21] Appl. No.: 30,059

[22] Filed: Apr. 13, 1979

[30] Foreign Application Priority Data

Apr. 17, 1978 [NL] Netherlands ............... 7804041

[51] Int. Cl.³ ............................................. H04M 1/05
[52] U.S. Cl. ............................................. 179/156 R
[58] Field of Search .................. 179/107 R, 156; 181/129, 131, 135, 137; D24/20

[56] References Cited

U.S. PATENT DOCUMENTS

| 1,568,721 | 1/1926 | Butcher et al. | 179/156 R |
| 1,775,204 | 9/1930 | Lucarelle | 179/156 R |
| 1,813,931 | 7/1931 | Johnson | 179/156 R X |
| 2,498,960 | 2/1959 | Mullin | 179/156R |
| 2,780,681 | 2/1957 | Shaper | 179/156 R |
| 2,827,514 | 3/1958 | Murray | 179/156 R |
| 3,532,837 | 10/1970 | Dyar et al. | 179/156 R |

Primary Examiner—Bernard Konick
Assistant Examiner—Aristotelis M. Psitos
Attorney, Agent, or Firm—William J. Streeter; Bernard Franzblau

[57] ABSTRACT

A stethoscopic headphone set comprising two identical arms each provided with an earphone, Which arms terminate in a hinged connecting element including a wire spring. The connecting element essentially comprises two mirror-symmetrical identical coupling members which cooperate with each other via a gear transmission and which fully enclose the wire spring. The wire spring may comprise two helical springs which are mirror-symmetrical, each helical spring being incorporated in a coupling member.

10 Claims, 3 Drawing Figures

STETHOSCOPIC HEADPHONE SET

The invention relates to a stethoscopic headphone set comprising two identical arms each provided with an earphone, which arms terminate in a hinged connecting element including a wire spring.

Such a headphone set is already known from Swiss Pat. No. 3343. The arms of this headphone set form part of a wire spring bent in the same manner as a safety pin.

In order to obtain an identical deflection of the two arms, the present invention is characterized in that a hinged connecting apparatus (element) essentially comprises two identical coupling members arranged in mirror image which cooperate with each other via a gear transmission and which fully enclose the wire spring.

This construction has the advantage that the tendency of the headphone set to become lopsided is substantially reduced and that an equal light pressure will be experienced on both of the ears of a user.

An embodiment of the invention is characterized in that the wire spring arrangement comprises two helical springs, which are mirror-symmetrical, each helical spring being incorporated in a coupling member.

Preferably, each coupling member comprises a disc which is provided with teeth along a part of its circumference so that said discs, i.e. coupling members, cooperate with each other via said teeth. Each disc has a cylindrical recess which is adapted to accommodate a respective one of the two helical springs with one tangentially extending end of the helical spring being retained behind a cam of the disc. An oblong mount for receiving an arm is secured to the disc.

The two helical springs can be manufactured from a single wire; for this purpose the two adjacently and mirror-symmetrically disposed ends are interconnected. In other words, a wire spring arrangement is provided for exerting a force on the arms of the headphone set and which comprises a wire spring having first and second helical spring parts with their axes in parallel and mechanically coupled to first and second disc-shaped coupling members, respectively, and wherein said axes coincide with the axes of rotation of the corresponding coupling members, respectively. Each coupling member may include a recess in which the respective spring part is located. By having one of the coupling members cooperate with a switch in the supply lead to the headphone set, the earphones can be switched off in a rest position.

By way of example, an embodiment of the invention will be described in more detail with reference to the accompanying drawings.

Figure 2:
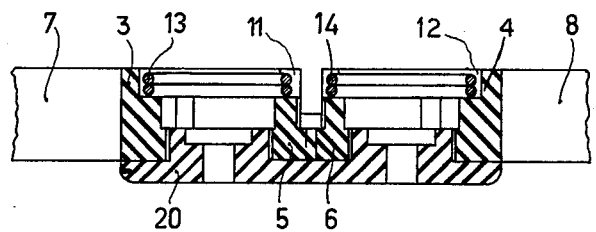
Figure 3:
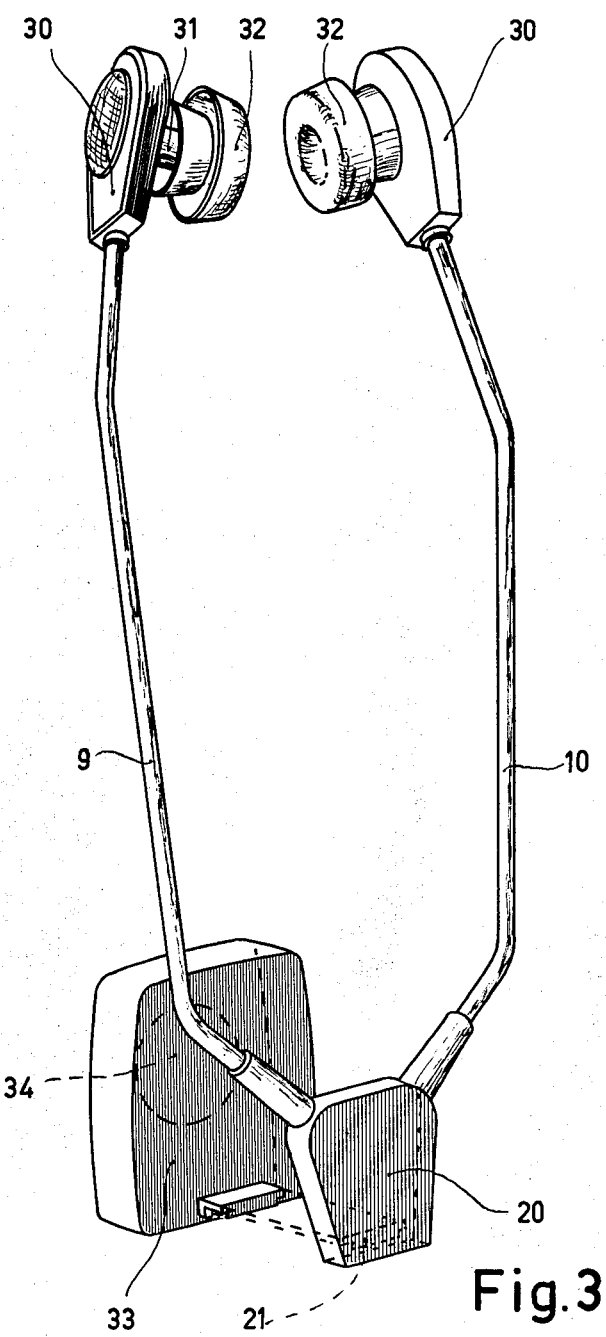

In the drawings:

FIG. 1 is a longitudinal sectional view of a headphone set showing the connecting element in accordance with the invention, FIG. 2 is a cross-sectional view taken on the line II—II of FIG. 1, and FIG. 3 is an exploded view of the headphone set.

In FIGS. 1 and 2, which are depicted on an enlarged scale, the coupling members 1 and 2 are constructed and arranged mirror-symmetrically. Each coupling member comprises a disc 3 and 4 respectively, which is provided with teeth 5 and 6 respectively over an angle of approximately 120° along the circumference. These discs 3, 4 constitute a linking gear transmission which is effective through this angle.

Furthermore, the discs 3, 4 are provided with tapered tubular mounts 7 and 8 respectively, in which mounts tubular metal arms 9 and 10 are clamped.

The other ends (see FIG. 3) of the arms are each provided with an earphone 30, which in this example is a mini-electret capacitor loudspeaker. The sound of each earphone 30 is transmitted to the ear of the person wearing it via a perforated ball-joint 31 and an earphone 32 which is secured thereto.

Each disc 3 and 4 has on one major surface a cylindrical recess 11 and 12 respectively, in which the cylindrical helical springs 13, 14 are mounted, respectively. The axis of spring 13 coincides with the axis of the disc 3, i.e. the axis of coupling member 1, whereas the axis of spring 14 coincides with the axis of disc 4 or coupling member 2. The two helical springs 13 and 14 are manufactured from a single piece of wire. The spring ends 15, 16 are disposed behind associated cams 17, 18, which form a part of the discs 3, 4. The other ends of the springs constitute a kinked connection spring 19.

The coupling members 1 and 2 are accommodated in a flat thin-walled housing 20 which consists of two shells. This housing furthermore comprises a number of electrical connectors 21, to which the two earphones are connected by leads via arms 9, 10 and coupling members 1 and 2 (leads not shown).

This connector includes a microswitch 22 which cooperates with the coupling member 1 and which is open in the rest position, that is when the arms 9 and 10 are disposed nearest one another, and which is closed in the operating position, that is with the arms in the spread position.

In the first (rest) position the earphones are disconnected from the electrical connectors 21.

In FIG. 3 an additional box 33 which contains an infrared receiver 34 is depicted for use in a system that includes a transmitter operating at frequencies in the infrared frequency domain. This box may be connected to the same connector 21 as the lead for direct connection to for example an associated dictation machine.

The wire spring arrangement exerts a force on the arms that counteracts the deflection of the arms 9 and 10. This deflection is the same for each of the arms and can be adjusted very smoothly as a result of the gear transmission which is provided.

What is claimed is:

1. A stethoscopic headphone set comprising, a pair of arms which terminate in a hinged connecting apparatus including a wire spring arrangement comprising two helical springs which are mirror-symmetrical and with each arm provided with an earphone, the connecting apparatus comprising two identical disc-shaped coupling members arranged in mirror image and each provided with teeth along a part of its periphery so that said coupling members cooperate with each other via said teeth, and wherein each helical spring is located in a coupling member such that the axis of each spring coincides with the axis of a corresponding coupling member.

2. A headphone set as claimed in claim 1 wherein each disc-shaped coupling member includes a cylindrical recess on one major surface adapted to house the corresponding helical spring, one tangentially extending end of the helical spring being retained behind a cam situated on the disc-shaped coupling member, and an oblong member secured to the coupling member for receiving an arm.

3. A headphone set as claimed in claims 1 or 2 wherein the two helical springs comprise one wire with two adjacent ends of the two helical springs being interconnected.

4. A headphone set as claimed in claims 1 or 2 wherein one of the coupling members co-operates with a switch which is connected in a supply lead to the earphones.

5. A headphone set comprising, a pair of tubular arms extending at an angle to one another from a hinged connecting apparatus that comprises first and second disc-shaped coupling members each provided with teeth along a part of its periphery so that said coupling members mechanically cooperate with each other via said teeth, a wire spring arrangement for exerting a force on said arms and comprising at least one wire spring means having first and second helical spring parts with their axes in parallel and mechanically coupled to said first and second coupling members, respectively, and an earphone coupled to a free end of one of said arms.

6. A headphone set as claimed in claim 5 wherein the axes of said first and second helical spring parts coincide with the axes of rotation of the corresponding first and second disc-shaped coupling members, respectively, and each coupling member includes a recess in which the respective spring part is located.

7. A headphone set as claimed in claims 5 or 6 wherein the coupling members and the wire spring means are arranged so that the wire spring arrangement counteracts the deflection of said pair of arms.

8. A headphone set as claimed in claims 5 or 6 wherein said first and second helical spring parts of the wire spring means comprise first and second individual helical springs which are mirror-symmetrical.

9. A headphone set as claimed in claims 5 or 6 wherein said wire spring means comprises a single wire with said first and second helical spring parts forming an integral part thereof.

10. A headphone set as claimed in claims 5 or 6 wherein each of said first and second helical spring parts includes a projecting end portion, the headphone set further comprising a pair of projection members arranged so as to retain said end portions of the first and second helical spring parts.

* * * * *